United States Patent [19]

O'Neill

[11] Patent Number: 4,769,511
[45] Date of Patent: Sep. 6, 1988

[54] ALKYLATION PROCESS UTILIZING ENHANCED BOILING SURFACE HEAT EXCHANGER IN THE REACTION ZONE

[75] Inventor: Patrick S. O'Neill, Williamsville, N.Y.

[73] Assignee: Union Carbide Corporation, Danbury, Conn.

[21] Appl. No.: 221,985

[22] Filed: Mar. 5, 1987

[51] Int. Cl.$^4$ ................................. C07C 2/54
[52] U.S. Cl. .................... 585/715; 165/133; 585/719; 585/720
[58] Field of Search ............ 585/715, 719, 720, 731; 165/133

[56] References Cited

U.S. PATENT DOCUMENTS

| | | | |
|---|---|---|---|
| 2,949,494 | 8/1960 | Putney | 585/715 |
| 3,168,591 | 2/1965 | Beavon et al. | 585/715 |
| 4,060,125 | 11/1977 | Fujie et al. | 165/133 |
| 4,064,914 | 12/1977 | Grant | 165/133 |
| 4,216,826 | 8/1980 | Fujikake | 165/133 |
| 4,293,729 | 10/1981 | Kolb et al. | 585/715 |
| 4,478,276 | 10/1984 | Rosenbaum et al. | 165/133 |

Primary Examiner—Asok Pal
Attorney, Agent, or Firm—Morris N. Reinisch

[57] ABSTRACT

The present invention is directed to an improvement in an alkylation process involving effluent refrigeration in which an enhanced boiling surface heat exchanger is utilized in the alkylation reaction zone so as to carry out the reaction at its optimum reaction temperature and at a positive compressor suction pressure.

15 Claims, 1 Drawing Sheet

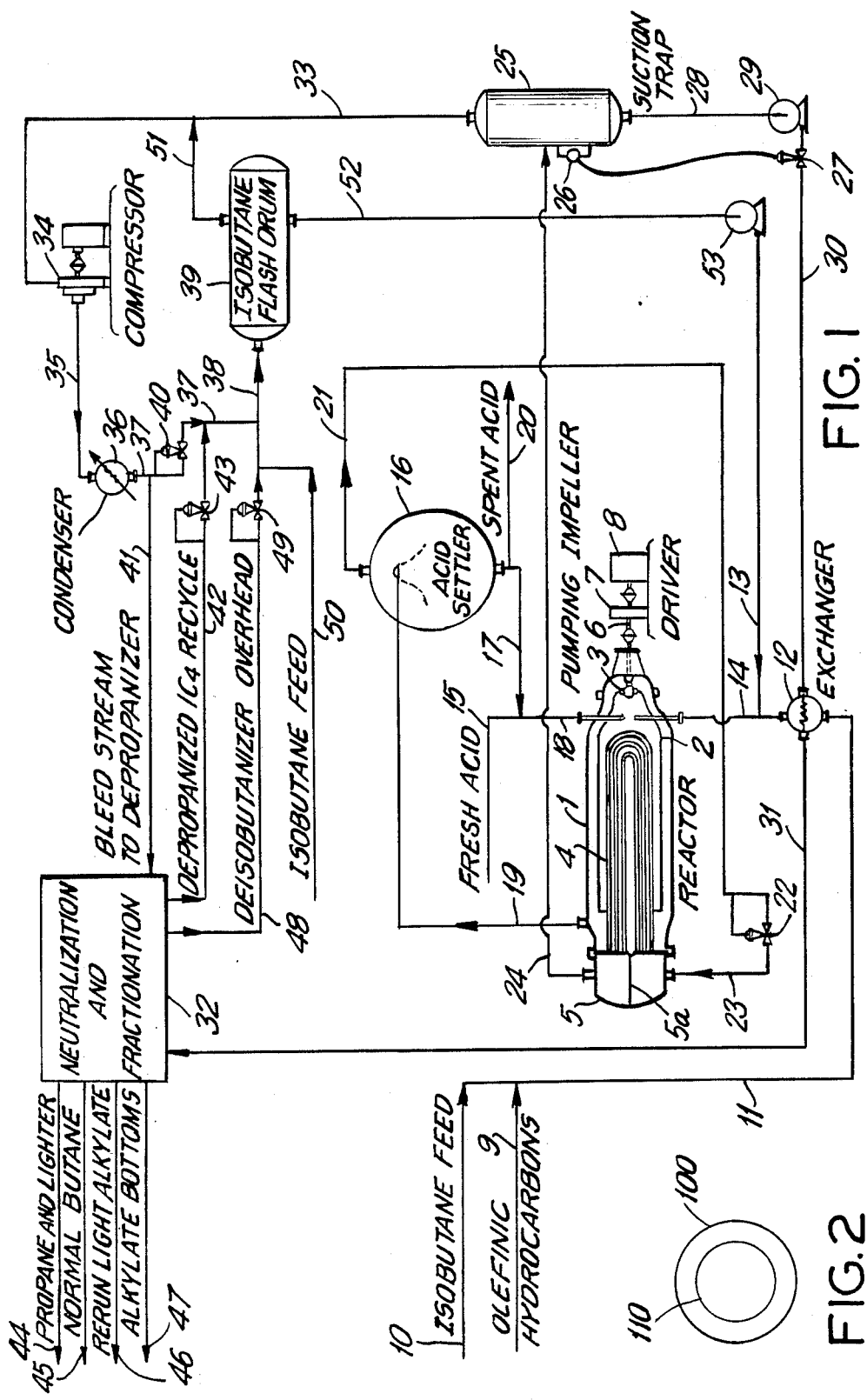

ALKYLATION PROCESS UTILIZING ENHANCED BOILING SURFACE HEAT EXCHANGER IN THE REACTION ZONE

BACKGROUND OF THE INVENTION

1. Field of the Invention

This invention pertains to the field of alkylating isoparaffinic hydrocarbons with olefinic hydrocarbons in the presence of an acid catalyst including the use of effluent refrigeration. More specifically, the present invention relates to the use of enhanced boiling surface on the inside surface area of the chiller tubes within the reaction zone.

2. Discussion of Related Art

Alkylation in the petroleum refining industry involves the chemical reaction of isoparaffinic hydrocarbons with olefinic hydrocarbons, typically isobutane with isobutylene, in the presence of a catalyst such as sulfuric or hydrofluoric acid, to product $C_8$ branched hydrocarbons such as trimethylpentanes (iso-octanes). These higher molecular weight "alkylates", as they are called, improve the anti-knock properties of motor gasoline. The increased use of unleaded fuels has considerably increased the importance of the alkylation process within the refining industry.

Alkylation has been commercially practiced for more than fifty years, and is competitive with other octane enhancement processes when there is a ready supply of isobutane and isobutylene. Generally, there are four different methods for carrying out the alkylation process today: sulfuric acid autorefrigeration, sulfuric acid-effluent refrigeration, hydrofluoric acid-time tank, and hydrofluoric acid tubular reactor. Of these four methods, only sulfuric acid-effluent refrigeration involves the boiling of refrigerant within a heat exchanger to cool the reaction zone. It is this method of alkylation with which the present invention is primarily directed. Reference is made to U.S. Pat. Nos. 2,664,452, 2,906,796 and 2,949,494 which describe such an alkylation technique and which are incorporated herein by reference.

The basic chemical reaction for isobutane and isobutylene in the presence of concentrated sulfuric acid at 40° to 55° F. is the following:

Generally, in the basic process, concentrated sulfuric acid is mixed with cracked gases containing olefinic components such as propylene and isobutylene as well as propane and butane in addition to both fresh and recycled isobutane in the reaction zone, with about 40% sulfuric acid being present by volume. The fluids are not miscible, and the $C_4$ fractions float on the acid. When the reactor is vigorously agitated, the hydrocarbons break up into extremely fine droplets, and an emulsion is formed which increases the rate of reaction. After about 1 hour at 45° F. and 70 psia, a yield of about 15% to 20% alkylate is obtained.

Temperature is a critical variable in the alkylation reaction. The lower the temperature, the less the tendency to form undesirable side reactions involving self alkylation of the isobutane, or reaction of the acid to form alkyl sulfates. Consequently, better quality alkylate and more conversion is obtained when the reaction is carried out at the lower temperature, with the lower limit being generally about 35° F. This lower limit is primarily set by the high viscosity of the acid at that temperature and the cost of the refrigeration reguired to remove the exothermic heat of reaction.

Since temperature is so important in the alkylation reaction and in view of the fact that the reaction is exothermic in nature, it is therefore necessary to continually remove the heat of reaction to maintain a desirable temperature of reaction. In order to do so, the sulfuric acid effluent refrigeration technique of alkylation involves continuously passing effluent from the reactor to a settler (while the reaction is going on) to separate the effluent into a hydrocarbon phase and an acid catalyst phase. The hydrocarbon phase is then reduced in pressure thereby lowering its temperature. This cooled stream, now containing both liquid and flashed vapor created by the pressure reduction, is then passed in indirect heat exchange relationship through the reaction zone thereby removing the heat of reaction. Typically, the cooled hydrocarbon stream passes through a U-shaped tube bundle chiller which is provided within the reaction zone. As the heat of reaction is transferred to the chiller, more of the liquid hydrocarbon vaporizes inside the chiller tubes.

The large amount of vapor generated by the heat of reaction in the hydrocarbon stream is separated from the liquid portion of the stream, typically in a suction trap. The liquid goes to a fractionation step, while the vapor passes through a compressor and condenser to form a further liquid phase. This further liquid phase is then throttled to an intermediate flash tank which is at the same pressure as the suction trap, both pressures being controlled by the suction pressure on the compressor. Flashed vapors are recycled to the compressor, while the liquid phase, known commonly in the art as "effluent refrigerant" and consisting primarily of isobutane, is recycled back to the reaction zone providing additional cooling of the reaction.

While the alkylation reaction is most desirably carried out at the optimum temperature range of from about 40° F. to 45° F., most commercial plants generally operate their alkylation reactors at the higher temperature of 50° F., and in some cases as high as 55° F. or higher, due to economical and safety factors.

More particularly, referring to the well known heat transfer equation:

$$Q = U \times A \times (T_{reactor} - T_{boiling\ fluid})$$

where Q is the heat generated by the heat of reaction in BTU/hr; U is the overall heat transfer coefficient in units of $(BTU/hr)/(ft^2 °F.)$; A is the surface area of the chiller in $ft^2$; $T_{reactor}$ is the temperature of the reaction; and $T_{boiling\ fluid}$ is the mean temperature of coolant hydrocarbon phase; it is seen that for a given heat duty Q, there are essentially four different parameters that can theoretically be varied in order to provide the necessary heat transfer.

Of all of these parameters, increasing the surface area of the chillers involves the most costly option. Due to practical design limitations of the chiller/reactor units, commonly known in the art as "contactors", a plurality of these contactors must be provided if a substantial amount of chiller surface area is needed. Aside from the capital costs involved in providing such additional contactors, there are a number of factors which come into play which add to the disadvantages of this approach. The first effect is that additional contactors each employ an additional agitator within each respective reaction zone. This now undesirably adds mechanical energy into the reaction zone which increases the heat load of the system. Of course, the costs associated in operating these additional contactors also increases. Secondly, the reactor space velocity decreases when employing a plurality of contactors, typically in parallel. This tends to increase the production of high boiling components, such as alkylates, within the reaction effluent which undesirably elevates the boiling temperature and reduces the temperature difference available for heat transfer. Finally, inasmuch as the chiller fluid has to pass through a greater number of contactors, the tube side velocity is reduced with a concomitant reduction in the inner tube heat transfer coefficient which in turn leads to a decrease in the overall coefficient. The net result of all of the above is that increasing the chiller surface area is not the most viable alternative.

The next alternative is to attempt to decrease the temperature of the boiling fluid, i.e., the fluid passing through the chiller, so as to provide a greater temperature gradient for the required heat transfer. This approach too is disadvantageous. As noted above, the boiling fluid is obtained by partially flashing the separated hydrocarbon phase coming from the acid settler to a reduced pressure. This reduced pressure is controlled by the suction pressure of the compressor in which the vaporized hydrocarbons within the boiling fluid are ultimately passed. As would be readily apparent to one skilled in the art, the temperature of the boiling fluid entering the chiller bundle is dependent upon the suction pressure of the compressor. By reducing the suction pressure, the temperature of the boiling fluid is correspondingly reduced. However, in order to provide a boiling fluid temperature which is low enough to establish a sufficient temperature gradient, the suction pressure of the compressor would undesirably have to operate under partial vacuum. Thus, if a system were operating at a reaction temperature of about 52° F. with the boiling fluid entering the chiller at 25° F. at a suction pressure of 17 psia, in order to reduce the reaction temperature to 42° F., for example, the chiller temperature would have to enter at a temperature of 15° F. which would require a compressor suction pressure of 13 psia, which is below atmospheric. Moreover, due to the lower boiling fluid temperature and pressure which leads to a decrease in the vapor density, more compressor power would be required to compress the same amount of vapor.

Accordingly, attempting to accommodate the heat duty of the system by reducing the boiling fluid temperature will lead to increased power consumption or require the use of a larger compressor. Most importantly, however, it will also lead to a compressor operating at a suction pressure under vacuum. This condition could lead to the leakage of air into the system and the potentially dangerous buildup of oxygen in the hydrocarbons.

Without simply increasing the reaction temperature in order to provide an increased temperature gradient, the only other variable in the heat transfer equation is U, the overall heat transfer coefficient. This overall heat transfer coefficient is well recognized by those skilled in the art as being dependent upon the combination of the individual liquid film heat transfer coefficient on the outside of the tube which is in contact with the reaction emulsion and the individual boiling film heat transfer coefficient on the inside of the tube which is in contact with the boiling fluid.

Due to the nature of the emulsion, it has been extremely difficult to measure and/or calculate an emulsion heat transfer coefficient for the outside of the chiller tubes. By using well established relationships, it is possible, however, to calculate the heat transfer coefficient for the inner, boiling side of the tube. Having established from existing operating systems that the overall heat transfer coefficient for the chiller in such an alkylation reaction is about 50 to 60 (BTU/hr)/(ft$^2$ °F.), and after calculating the heat transfer coefficient for the boiling fluid, it is possible to extract a heat transfer coefficient for the emulsion side of the chiller. See, for example, Chen, J. C., "Industrial and Engineering Chemistry, Process Design and Development", Vol. 5, No. 3, pp. 322 (1966) for methods of calculating in tube film coefficients.

Based upon what is conventionally known by one skilled in the art, it is generally believed that the controlling factor influencing the overall heat transfer coefficient is the emulsion heat transfer coefficient on the outside of the chiller. In other words, based on calculations such as that described above, the heat transfer coefficient on the emulsion side generally is believed to be lower than the heat transfer coefficient on the inner boiling side. Consequently, if one skilled in the art were to attempt to increase the overall heat transfer coefficient, he would seek to increase the emulsion side heat transfer coefficient.

However, due to the nature of the emulsion, the prior art has generally refrained from modifying the surface of the outer tube so as to attempt to increase the outside heat transfer coefficient. Thus, a common way of increasing the coefficient would be to add fins to the outer walls of the tubes. However, such extended surfaces would be susceptible to corrosion by the acid; fouling and clogging; and cause a decrease in the flow. As a result, one skilled in the art has stayed away from attempting to modify the overall heat transfer coefficient as a means of providing better heat transfer.

In view of the above, the skilled art worker has found essentially no choice in many cases but to carry out the alkylation reaction at a temperature which is higher than desirable or operate the suction pressure of the compressor as low as possible, even under vacuum, in order to provide the necessary temperature gradient for the required heat transfer. Clearly, a need exists to improve this alkylation process, particularly to be able to run the reaction at the most optimum temperature without the need to run the compressor suction pressure under vacuum.

SUMMARY OF THE INVENTION

Applicant has discovered an improvement in the sulfuric acid-effluent refrigeration alkylation process which eliminates or substantially reduces the disadvantages noted above.

More particularly, by virtue of Applicant's discovery, it is now possible to operate the alkylation reaction at a temperature which is less than 50° F., preferably at a temperature within the range of from 40° F. to 45° F. and at a compressor suction pressure which is greater than atmospheric pressure without having to alter flow rates or chiller heat transfer surface area. In fact, as a result of this invention, the capacity of the chiller can be increased for a given area and temperature gradient; the reactor temperature can be decreased for a given capacity and heat transfer area; and/or, the boiling fluid temperature can be increased thus increasing the compressor throughput or reduce its energy consumption.

Specifically, Applicant has discovered that the above features can be accomplished by utilizing an enhanced boiling surface chiller tube having a porous boiling surface on the inside of the tube. Such enhanced boiling surface tubes are well known and are available under the tradename High Flux tubes from Union Carbide Corporation, Danbury, Conn.

Quite surprisingly and unexpectedly, Applicant has discovered that in contradistinction to what is generally believed in the art, the controlling heat transfer coefficient in the chiller is actually on the inside of the tubes in which the boiling of the hydrocarbons takes place, and not on the outside of the tubes which is generally understood as being controlling. Thus, by providing an enhanced boiling surface in the inner tube, the overall heat transfer coefficient is surprisingly increased by a factor of as much as 2 to 2.5 or more leading to a substantial increase in the ability of the chiller to remove the heat of reaction from the reaction zone.

Such enhanced boiling surface heat exchange tubes are discussed in, for example, U.S. Pat. Nos. 3,384,154, 3,821,018, 4,064,914, 4,060,125, 3,906,604, 4,216,826 and 3,454,081 all of which are incorporated herein by reference. These enhanced tubes are made in a variety of different ways which are well known to those skilled in the art. For example, such tubes may comprise annular or spiral cavities extending along the tube surface made by mechanical working of the tube. Alternatively, fins may be provided on the surface. So too, the tubes may be scored to provide ribs, grooves, a porous layer and the like.

Generally, the more efficient enhanced tubes are those having a porous layer on the boiling side of the tube which can be provided in a number of different ways well known to those skilled in the art. In one such method, as described in U.S. Pat. No. 4,064,914, the porous boiling layer is bonded to one side of a thermically conductive wall. The porous boiling layer is made of thermally conductive particles bonded together to form interconnected pores of capillary size having equivalent pore radius of less than about 6.0 mils, and preferably less than about 4.5 mils. As used herein, the phrase "equivalent pore radius" empirically defines a porous boiling surface layer having varied pore sizes and non uniform pore configurations in terms of an average uniform pore dimension. Such an enhanced tube containing a porous boiling layer is commercially available under the tradename High Flux tubing made by Union Carbide Corporation, Danbury, Conn.

As essential characteristic of the porous surface layer is the interconnected pores of capillary size, some of which communicate with the outer surface. Liquid to be boiled enters the subsurface cavities through the outer pores and subsurface interconnecting pores, and is heated by the metal forming the walls of the cavities. At least part of the liquid is vaporized within the cavity and resulting bubbles grow against the cavity walls. A part thereof eventually emerges from the cavity through the outer pores and then rises through the liquid film over the porous layer for disengagement into the gas space over the liquid film. Additional liquid flows into the cavity from the interconnecting pores and the mechanism is continuously repeated.

By utilizing this enhanced boiling surface tubing containing a porous boiling layer, the boiling film heat transfer coefficient of the boiling fluid within the tubes is increased by a factor of about 10, typically to a value of about $1000 (BTU/hr)/(ft^2 °F.)$ or more. This is due to the fact that the heat leaving the base metal surface of the tube does not have to travel through an appreciable liquid layer before meeting a vapor-liquid surface producing evaporation. Within the porous layer, a multitude of bubbles are grown so that the heat, in order to reach a vapor liquid boundary, need travel only through an extremely thin liquid layer having a thickness considerably less that the minute diameter of the confining pore. Vaporization of the liquid takes place entirely within the pores.

When using an enhanced boiling surface other than a porous layer, the boiling film heat transfer coefficient is typically increased by a factor of about 4 or more to a value of at least about $400 (BTU/hr) (ft^2°F.)$ The utilization of this enhanced boiling surface tubing not only increases the overall heat transfer coefficient thereby increasing the available capacity of the chiller but, moreover, provides yet additional advantages.

Firstly, the use of this enhanced tubing permits the temperature of the boiling fluid within the chiller to enter at a higher temperature. Generally, the temperature of the boiling fluid can be increased, at a given temperature of reaction, by an amount of about 9° to 12° F., providing a temperature gradient between the boiling fluid and the reaction mixture of from about 10° to 20° F., preferably about 10° to 15° F. This increased boiling fluid temperature also leads to an increase in the boiling fluid pressure. This, in turn, reduces the energy consumption of the compressor. In general, a 10 degree increase in boiling fluid temperature reduces the power consumption of the compressor by about 12%. Finally, the increase in boiling fluid pressure enables the operation of the compressor suction to be greater than atmospheric, preferably from 0 to 7 psig, and most preferably in the range of from about 2 to 4 psig.

Once a portion of the extra heat transfer capability is utilized by increasing the temperature of the boiling fluid to ensure that the compressor suction is greater than atmospheric pressure, there is still generally yet additional heat transfer capability left to be effectively utilized. This extra cooling capacity can all be used to cool the reaction temperature to its optimum temperature or, alternatively, by keeping the reaction temperature constant, it can be used to increase the feed rate of the reactants to the reaction zone thereby producing more alkylate product. As still another alternative, the extra cooling capacity may be distributed between reducing the reaction temperature and increasing the throughput of the system.

By increasing the overall heat transfer coefficient, the temperature of the reaction can be operated at the optimum temperature. The effect of reactor temperature on alkylate quality is quite significant. For a 10 degree F. reduction in temperature, the octane number (RON) of the alkylate is increased by about 0.5 to 0.72 points. In addition, the lower temperature reduces the consumption of acid as well. Each 10 degree reduction in temperature reduces acid consumption of 0.08 lbs. of sulfuric acid per gallon of alkylate product. Still further, a decrease in reaction temperature would reduce the tendency for undesirable side reactions, and increase the amount and quality of alkylate product. Generally, the reaction temperature can be reduced to a temperature less than 50° F., preferably to a temperature of 40° to 45° F.

Although temperature of reaction is quite important, there may be times in which an increase in product output capacity is also important. As a result of the increased overall heat transfer coefficient and an increase in the boiling fluid temperature and pressure, the capacity of the chiller-compressor system can be increased by at least about 10%. Thus, at constant compressor power, as a result of the higher vapor temperature entering the compressor which in turn leads to a higher vapor density, more vapor is compressed and condensed on a weight basis providing for improved chiller capacity. By operating the suction pressure of the compressor at maximum, typically about 6 psig, and carrying out the reaction at a maximum temperature of about 55°–58° F., the increase in the capacity of the system is about 15 to 20%.

BRIEF DESCRIPTION OF THE DRAWINGS

FIG. 1 is a schematic flow diagram of one embodiment of the present invention showing an acid-effluent refrigeration alkylation process utilizing an enhanced chiller tube within the contactor.

FIG. 2 is a cross section of one of the chiller tubes used in the contactor of FIG. 1.

DETAILED DESCRIPTION OF THE INVENTION

Referring to FIG. 1, at 1 is a reactor shell equipped with an open-ended circulating tube 2. In one end of the circulating tube is a propeller or pump impeller 3 and within the circulating tube is a chiller consisting of a tube bundle 4 having internal enhanced boiling surface provided with a distributing head 5 which encloses one end of the reactor. The impeller is mounted on a shaft 6 rotated through a reduction gear 7 by any suitable means such as an electric motor or steam turbine shown diagrammatically as 8.

Circulation within the reactor is established by the impeller through the annular space between the shell and circulating tube 2 over the cooling tubes 4 and back to the impeller.

Olefinic hydrocarbons and isoparaffinic hydrocarbons, such as isobutane, are introduced to the system through lines 9 and 10, respectively, being combined in feed line 11 prior to passage through heat exchanger 12. Recycled isobutane returned through line 13 is introduced into the feed in line 14. Fresh acid, such as sulfuric acid, is fed to the reactor through line 15 and recycle acid from settler 16 is returned through line 17. The hydrocarbons supplied through lines 9 and 10 mixed with recycled isobutane added through line 13 are mixed in the reactor with the acid catalyst introduced through lines 15, 17 and 18.

Alkylation of the isoparaffinic hydrocarbons by the olefinic hydrocarbons takes place in the reactor 1, while the mixture is being rapidly circulated and agitated by impeller 3 insuring a thorough and intimate mixture of the hydrocarbons with acid catalyst. The mixture of hydrocarbons and acid is discharged from the reactor through line 19 passing to the acid settler 16 where it is permitted to separate into a heavier acid phase and a hydrocarbon phase. The acid phase is recycled to the suction side of the pumping side of impeller 3 of the reactor through line 17, while a portion of the acid separated in the settler may be discarded through the spent acid discharge line 20 to maintain a proper balance and proportioning of catalyst and reactants in the system.

The hydrocarbon phase separated in the settler is discharged from the top of the settler through line 21, and pressure upon these hydrocarbons is reduced by throttling at valve 22, after which the liquid/vapor mixture is passed immediately through line 23 to the distributing head 5 of the reactor. The head 5 is divided by a partition 5a which causes the coolant to pass through the heat exchange elements or enhanced tube bundle 4, then into the opposite side of the distributing head and out through line 24. The temperature of the reaction will generally be less than 50° F., and preferably in the range of from about 40° F. to 50° F., and most preferably in the range of 40° to 45° F.

Upon passing valve 22, pressure on the hydrocarbon phase of the effluent is reduced to the order of 0 psig to 10 psig, preferably 2 to 4 psig, causing a considerable portion of the lighter components of the effluent to vaporize and resulting in the cooling of the entire hydrocarbon effluent mixture. Depending upon the pressure established within the tube bundle 4 of the reactor, the temperature of the hydrocarbon effluent phase will be reduced to be in the range of from about 15° to 25° F. by the reduction of pressure. This chilled effluent, which is a mixture of liquid and vapor, while passing through the enhanced chiller tubes 4 of the reactor absorbs the exothermic heat of alkylation reaction by indirect heat exchange resulting in vaporization of additional lighter components of the effluent.

Upon leaving the chiller tubes 4 of the reactor, the partially vaporized effluent passes from the opposite side of the circulating head through line 24 to suction trap 25 where the vapor and liquid portions of the effluent are separated. A liquid level control 26 manipulating valve 27 regulates the discharge of the liquid phase from the suction trap through line 28. This liquid is returned by pump 29 through line 30 to heat exchanger 12 where it is is brought in heat exchange relation with the incoming feed stock. From the heat exchanger, the liquid passes through line 31 to the neutralization and fractionation steps diagrammatically shown as 32.

The vapors separated from the effluent in suction trap 25 pass out through line 33 to compressor 34 from which they are discharged through line 35 to condenser 36 where they are totally condensed. A portion of the condensate from condenser 36 is directed through lines 37 and 38 to isobutane flash drum 39 which is operated at the same pressure as suction trap 25, both pressures being controlled by the suction pressure on compressor 34 which, in accordance with the present invention operates at a pressure which is greater than atmospheric and is equal to the pressure of the hydrocarbon phase after passing valve 22. Interposed in line 37 is a pressure reducing valve 40 which holds sufficient back pressure on the condenser 36 to make possible total condensation of the hydrocarbons. Liquid hydrocarbons passing through valve 40 are thereby reduced in pressure causing partial vaporization and chilling of the hydrocarbons prior to their introduction into flash drum 39.

When propane is a component of any of the feed streams, a portion of the condensate withdrawn through line 37 is diverted through line 41 to the depropanizer of the fractionation section 32. After depropanization, this stream is returned to the system through line 42, pressure reducing valve 43 and lines 37 and 38 to the isobutane flash drum 39. Back pressure valve 43 in line 42 functions in the same manner as reducing valve 40 described above.

The liquid hydrocarbons withdrawn from suction trap 25 and passed to fractionation are there separated into streams of propane, normal butane, light alkylate and alkylate bottoms. The product streams are normally removed from the system through lines 44, 45, 46 and 47, respectively. The isobutane stream taken overhead from the deisobutanizer tower is recycled through line 48, reduction valve 49 and line 38 to the isobutane flash drum from which it is directed to the reaction zone in reactor 1. Fresh isobutane feed to the system may also be brought in either through line 10 or through line 50 which connects through line 38 to the isobutane flash drum. All of the streams entering the isobutane drum 39 are subjected to reduced pressure established by the suction of the compressor and are thereby self-refrigerated. The vapors evolved in the isobutane flash drum by this self-refrigeration are passed through line 51 to the compressor, while the chilled liquid from the drum, principally isobutane, is directed through line 52 to pump 53 and then through lines 13 and 14 to the reactor.

FIG. 2 depicts a cross section of the enhanced chiller tubes in which outer surface 100 contacts the reaction mixture and inner surface 110, containing the preferred enhancement of a porous layer, contacts the boiling fluid.

The preferred enhanced tube for use in the alkylation contactor ranges in diameter from 0.75 to 1.25 inch, with 1.0 inch being most common. The tube wall thickness ranges in thickness from 0.08 to 0.15 inch, with 0.10 being preferred. Although the tube material may be comprised of any thermally conductive material, ferrous or stainless alloy is commonly used, the preferred material being ordinary carbon steel.

EXAMPLE

A comparison is made of two process conditions for the sulfuric acid alkylation reaction, one using contactor bundles with High Flux tubing, and the other with conventional tubes. In this example, a typical 10,000 barrel per stream per day (BPSD) in a plant having four contactors operating in parallel with two settling tanks are employed. Each settler is fed by two contactors. The total olefin and isobutane feed flow is 66,000 BPSD, while the refrigeration compressor (approximately 6,000 hp) has a suction pressure fixed at 17 psia, to avoid vacuum operation.

The details of the comparison are shown in Table I below. Each of the four contactors has a volume of 13,000 gallons, and a chiller bundle with a heat transfer area of 8,500 ft$^2$. The volume of each of the acid settler is 92,000 gallons. A high rate of internal circulation of the emulsion is maintained by impellers with a total power consumption of 1,200 hp. The total heat of reaction, including energy imparted to the fluid, is 41 million BTU/hr. Hydrocarbon from the settler is throttled and fed to the boiling side of the chiller. To remove the heat of reaction, the boiling flow, at 540,000 lb/hr, is approximately 50% vaporized. The boiling stream containing about 18% $C_8$ alkylate, enters at 25° F. and exits at 35° F. In order to maintain enough temperature difference to transfer the heat of reaction, consistent with an overall heat transfer coefficient of about 100 (BTU/hr)/(ft$^2$ ° F.) when utilizing High Flux tubing, and 50 (BTU/hr)/(ft$^{2°}$ F.) when using a bare tube bundle, the reactor temperature must be maintained at 43° F. and 55° F., respectively.

As seen in Table I, the relative octane number (RON) increases about 0.7 points, due to the lower reactor temperature, for the case using the High Flux tube bundle. In the examples, the reactor volume per BPSD of alkylate product is that typically used in commercial practice, namely, 4 to 4.5 gallons.

Case 3 in Table I illustrates the effect of attempting to lower the reactor temperature by adding more contactors. Since the overall coefficient for the High Flux tube bundle is about two times higher than for the bare tubes, it is assumed that doubling the number of bare tube contactors would reduce the reactor temperature to 43° F., the value achieved by the High Flux tubes. In reality, several additional effects occur which tend to make the necessary area increase even greater than two fold. The first effect is that an additional 1200 hp mechanical energy enters the circulating fluid from the impellors and must be removed. This increases the heat load to about 44 million BTU/hr. Since the boiling flow is fixed, more must vaporize which increases the outlet temperature. The second effect is that the reactor space velocity decreases which tends to increase the conversion or yield of $C_8$ alkylate, and thus the boiling temperature of the mixture. A third effect is that the total boiling flow of 540,000 lb/hr is now distributed over eight or more bundles rather than four, which at least halves the tube side velocity and reduces the tube side heat transfer coefficient. The net result is that considerably more than double the number of reactors must be added which is not feasible in an existing plant.

TABLE I

| | | | CASE 3 | |
| | | CASE 2 | CONV'T. TUBES | |
| | CASE 1 | CONVENTIONAL | REACTOR AT | |
| ITEM | HIGH FLUX | TUBES | TEMP-CASE 1 | REMARKS CASE 3 |
| --- | --- | --- | --- | --- |
| Alkylate Capacity BPSD | 10,000 | 10,000 | 10,000 | Fixed |
| Total Feed Flow BPSD | 66,000 | 66,000 | 66,000 | Fixed |
| No. Chillers in Parallel | 4 | 4 | 8+ | High |
| Volume of Each Chiller Gal. | 13,000 | 13,000 | 13,000 | Fixed |
| Area (Heat Transfer/ Chiller Ft.$^2$ | 8,500 | 8,500 | 8,500 | Fixed |
| No. Acid Settlers | 2 | 2 | 4 | Doubled |
| Volume of Settler, Gal. | 92,000 | 92,000 | 92,000 | Fixed |
| Space Velocity, BPSD Feed/ Barrels Reactor Volume | 53 | 53 | 26 | Equals (42 gal/bbl) (66,000)/(13,000) × (no. chillers) |
| % Alkylate in Boiling Feed | 18 | 18 | 20%+ | Because space velocity decreased |
| Total Flow to Boiling Side, #/hr. | 540,000 | 540,000 | 540,000 | Fixed |
| Amount Vaporized, Boiling Side % | 50 | 50 | Approx. 60+ | Increases because heat load increased |
| Total Contactors Heat Duty MMBTU | 41.0 | 41.0 | 44+ | Duty increased because of increased |

TABLE I-continued
EXAMPLE OF IMPROVED 10,000 BPSD ALKYLATION PROCESS USING HIGH FLUX

| ITEM | CASE 1 HIGH FLUX | CASE 2 CONVENTIONAL TUBES | CASE 3 CONV'T. TUBES REACTOR AT TEMP-CASE 1 | REMARKS CASE 3 |
|---|---|---|---|---|
| Agitator Power (Total) HP | 1,200 | 1,200 | 2,400+ | agitator power Increased because # of reactors increased |
| Boiling Inlet Temp. °F. | 25 | 25 | 28+ | Increased because alkylate increased |
| Boiling Outlet Temp. °F. | 35 | 35 | 40+ | Increased because alkylate and amount of vapor increased |
| Compressor Suction PSIA | 17 | 17 | 17 | Vacuum operation avoided |
| Reactor Temp. °F. | 43 | 55 | 43 | Not feasible |
| Mean ΔT °F. | 12.3 | 24.6 | <12° | Decreased because of alk. & % vapor increase |
| Overall Coeff., (Design) | 98 | 49 | <49 | Because of decreased boiling flow/chiller |
| Relative Octane # Increase | 0.72 | 0 | 0.72 | Only if reactor is at 43° F. |
| Reactor Volume/BPSD Used | 5.2 | 5.2 | 10.4+ | At least doubled |
| Reactor volume/BPSD Trade Practice | 4.0–4.5 | 4.0–4.5 | | |
| Reactor Area/Ratio Ft.$^2$/BPSD | 3.4 | 3.4 | 6.8+ | |
| Residence Time, Sec. | 1,630 | 1,630 | 3,260+ | |

What is claimed is:

1. In a process of alkylating isoparaffinic hydrocarbons with olefinic hydrocarbons in the presence of an acid catalyst comprising the steps of reacting isoparaffinic hydrocarbons and olefinic hydrocarbons in the presence of acid catalyst in a reaction zone to form alkylate, withdrawing a mixture of hydrocarbons with acid catalyst as effluent from said reaction zone, separating said effluent into an acid phase and a hydrocarbon phase in a first separating zone, reducing the pressure on the hydrocarbon phase to refrigerate it and vaporize volatile hydrocarbons, passing the refrigerated hydrocarbon phase in indirect heat exchange with the reaction mixture of hydrocarbons and catalyst in the reaction zone to remove exothermic heat of reaction and vaporize further volatile hydrocarbons in the hydrocarbon phase, said indirect heat exchange having an overall heat transfer coefficient $U_o$, separating the liquid portion of the hydrocarbon phase from the vapor portion thereof in a second separating zone, fractionating the liquid portion of the hydrocarbon phase to remove alkylate, passing the vapor phase material removed in said second separating zone through a compressor and a condenser to compress and condense the vapor phase to form a liquid phase, reducing the pressure on the liquid phase to refrigerate it and vaporize volatile hydrocarbons forming an isoparaffinic hydrocarbon liquid phase and a volatile hydrocarbon vapor phase, separating the refrigerated isoparaffinic hydrocarbon liquid phase from the volatile hydrocarbon vapor phase in a third separating zone, and adding the separated refrigerated isoparaffinic hydrocarbon liquid phase as a reactant in the reaction zone, the improvement which comprises:

(a) operating the said compressor at a suction pressure greater than atmospheric pressure, which suction pressure is equal to the pressure within the second and third separation zones;

(b) carrying out the reaction within the reaction zone at a temperature less than 50° F.; and (c) providing heat exchange apparatus having a thermally conductive wall with an enhanced boiling surface on one side of such wall for carrying out the indirect heat exchange of the refrigerated hydrocarbon phase with the reaction mixture, wherein the refrigerated hydrocarbon phase is in contact with the said enhanced boiling surface during the indirect heat exchange, and the overall heat transfer coefficient $U_o$ is increased by a factor of from about 2.0 to about 2.5.

2. The process of claim 1, wherein the enhanced boiling surface is a porous boiling layer.

3. The process of claim 1, wherein the enhanced boiling surface provides a boiling film heat transfer coefficient of greater than 400 (BTU/hr) (ft$^2$°F.).

4. The process of claim 2, wherein the porous boiling layer provides a boiling film heat transfer coefficient of greater than 1000 (BTU/hr) (ft.$^2$ °F.)

5. The process of claim 1, wherein the suction pressure of the compressor is in the range of from 0 to 7 psig.

6. The process of claim 5, wherein the suction pressure of the compressor is in the range of from 2 to 4 psig.

7. The process of claim 1, wherein the reaction temperature is in the range of from 40° to 45° F.

8. The process of claim 1, wherein the difference in temperature between the refrigerated hydrocarbon phase and the reaction mixture during the indirect heat exchange is in the range of from 10° to 20° F.

9. The process of claim 8, wherein the temperature difference is in the range of from 10° to 15° F.

10. The process of claim 1, wherein the overall heat transfer coefficient is increased to a value of from about 100 to about 125 (BTU/hr) (ft$^2$°F.).

11. In a process of alkylating isoparaffinic hydrocarbons with olefinic hydrocarbons in the presence of an acid catalyst comprising the steps of reacting isoparaffinic hydrocarbons and olefinic hydrocarbons in the presence of acid catalyst in a reaction zone at a first reaction temperature to form alkylate, withdrawing a mixture of hydrocarbons with acid catalyst as effluent from said reaction zone, separating said effluent into an acid phase and a hydrocarbon phase in a first separating zone, reducing the pressure on the hydrocarbon phase to refrigerate it and vaporize volatile hydrocarbons, passing the refrigerated hydrocarbon phase in indirect heat exchange with the reaction mixture of hydrocarbons and catalyst in the reaction zone to remove exothermic heat of reaction and vaporize further volatile hydrocarbons in the hydrocarbon phase, said indirect heat exchange having an overall heat transfer coefficient $U_o$, separating the liquid portion of the hydrocarbon phase from the vapor portion thereof in a second separating zone, fractionating the liquid portion of the hydrocarbon phase to remove alkylate, passing the vapor phase material removed in said second separating zone through a compressor and a condenser to compress and condense the vapor phase to form a liquid phase, reducing the pressure on the liquid phase to refrigerate it and vaporize volatile hydrocarbons forming an isoparaffinic hydrocarbon liquid phase and a volatile hydrocarbon vapor phase, separating the refrigerated isoparaffinic hydrocarbon liquid phase from the volatile hydrocarbon vapor phase in a third separating zone, and adding the separated refrigerated isoparaffinic hydrocarbon liquid phase as a reactant in the reaction zone, wherein the isoparaffinic hydrocarbons and olefinic hydrocarbons are fed to the reaction zone at a first feed rate in barrels/hr per square foot of indirect heat exchange surface area, the improvement which comprises:

(a) providing heat exchange apparatus having a thermally conductive wall with an enhanced boiling surface on one side of such wall for carrying out the indirect heat exchange of the refrigerated hydrocarbon phase with the reaction mixture, wherein the refrigerated hydrocarbon phase is in contact with the enhanced boiling surface during the indirect heat exchange and the overall heat transfer coefficient $U_o$ is increased by a factor of from about 2.0 to about 2.5;

(b) operating the said compressor at a suction pressure greater than atmospheric pressure, which suction pressure is equal to the pressure within the second and third separation zones; and (c) increasing the combined feed rate of isoparaffinic hydrocarbons and olefinic hydrocarbons to the reaction zone by an amount equal to at least 10% of the said first feed rate at a reaction temperature which is equal to or less than the said first reaction temperature.

12. The process of claim 11, wherein the enhanced boiling surface is a porous boiling layer.

13. The process of claim 11, wherein the enhanced boiling surface provides a boiling film heat transfer coefficient of greater than 400 (BTU/hr)/(ft$^2$°F.).

14. The process of claim 12, wherein the porous boiling layer provides a boiling film heat transfer coefficient of greater than 1000 (BTU/hr) (ft$^2$°F.)

15. The process of claim 11, wherein the overall heat transfer coefficient is increased to a value of from about 100 to about 125 (BTU/hr) (ft$^2$°F.).

* * * * *

UNITED STATES PATENT AND TRADEMARK OFFICE
CERTIFICATE OF CORRECTION

PATENT NO. : 4,769,511
DATED : September 6, 1988
INVENTOR(S) : Patrick S. O'Neill It is certified that error appears in the above-identified patent and that said Letters Patent is hereby corrected as shown below:

On the title page, the Serial No. "221,985" should properly read --021,985--.

Signed and Sealed this

Fourth Day of April, 1989

Attest:

DONALD J. QUIGG

*Attesting Officer*  *Commissioner of Patents and Trademarks*